United States Patent
Burka et al.

[11] Patent Number: 6,141,100
[45] Date of Patent: Oct. 31, 2000

[54] IMAGING ATR SPECTROMETER

[75] Inventors: E. Michael Burka, Winchester; Raul Curbelo, Lexington, both of Mass.

[73] Assignee: Bio-Rad Laboratories, Inc., Hercules, Calif.

[21] Appl. No.: 09/116,191

[22] Filed: Jul. 15, 1998

Related U.S. Application Data

[60] Provisional application No. 60/055,746, Aug. 15, 1997.

[51] Int. Cl.$^7$ ...................................................... G01J 3/45
[52] U.S. Cl. ........................ 356/346; 356/300; 356/326; 250/339.11
[58] Field of Search ..................................... 356/326, 328, 356/300, 445–448, 244, 346, 128, 135, 136, 237; 250/341.1, 339.11

[56] References Cited

U.S. PATENT DOCUMENTS

| | | |
|---|---|---|
| 4,681,451 | 7/1987 | Guerra et al. ............................ 356/373 |
| 5,106,196 | 4/1992 | Brierley . |
| 5,347,364 | 9/1994 | Kawasaki et al. . |
| 5,446,534 | 8/1995 | Goldman . |

FOREIGN PATENT DOCUMENTS

| | | |
|---|---|---|
| 0 516 481 | 5/1992 | European Pat. Off. . |
| 2148024 | 5/1985 | United Kingdom . |
| 90/05295 | 5/1990 | WIPO . |

OTHER PUBLICATIONS

Sweedler; "High... Detectors" Analytical Chemistry, vol. 60, No. 4 Feb. 15, 1988.

Beer, Reinhard, "Remote Sensing by Fourier Transform Spectrometry," CP430, *Fourier Transform Spectroscopy*: 11th *International Conference*(ed. J.A. de Haseth); 1998 The American Institute of Physics I–56396–746–4/98, PP. 170–186.

Bhargava, Rohit et al., "FT–IR Imaging of the Interface in Multicomponent Systems Using Opical Effects Induced by Differences in Refractive Index, " *Applied Spectroscopy*, vol. 52(3): pp. 323–328 (1998).

Chalmers, John M. et al., "Fourier Transform Infrared Microscopy: Some Advances in Techniques for Characterisation and Structure–Property Elucidations of Industrial Material, " Analyst, vol. 123, pp. 579–586 ( Apr. 1998).

Ciurczak, Emil W., "3–D Hyperspectral Infrared Biomedical Imaging, " Spectroscopy 14(1); pp. 12–15 (1999).

Colarusso, Pina et al., "Inrared Spectroscopy Imaging: From Planetary to Cellular Systems,"*Applied Spectroscopy*, vol. 52(3), pp. 106A–120A (1998).

Kidder, Linda H. et al., "Infrared Spectroscopic Imaging Microscopy: Applications to Biological Systems, "CP430, *Fourier Transform Spectroscopy: 11th International Conference*(ed. J.A. de Haseth); 1998 The American Institute of Physics I–56396–746–4/98, pp. 148–158.

(List continued on next page.)

*Primary Examiner*—F. L. Evans
*Attorney, Agent, or Firm*—Townsend and Townsend and Crew LLP

[57] ABSTRACT

Method and apparatus for providing an imaging attenuated total reflection (ATR) spectrometer which provides faster measurement speed and better spatial resolution than systems collecting an equivalent amount of data using conventional, non-imaging ATR methods and systems. Apparatus includes a radiation source, an interferometer coupled to the radiation source which produces a spectrally-multiplexed input beam of radiation, an internal reflection element (IRE) engaging a sample-under-test, a focal plane array detector, a first optical system adapted and positioned to direct and concentrate the input beam through the rear surface of the IRE towards a contact area of the sample such that an angle of incidence of said input beam at the front surface is equal to or greater than the critical angle for the IRE, and a second optical system adapted and positioned to collect reflected radiation from the contact area and image the same onto the focal plane array detector.

18 Claims, 5 Drawing Sheets

OTHER PUBLICATIONS

Kidder, L.H. et al., "Mercury Cadmium Telluride Focal–Plane Array Detection for Mid–Infrared Fourier–Transform Spectroscopic Imaging, " *Optics Letters,* vol. 22(10), pp. 742–744 (May 15, 1977) (Optical Society of America).

Koenig, J.L. et al., "Fast FT–IR Imaging: Theory and Applications,"Spectroscopy 13(1); pp. 22–28 (Nov. 1998).

Marcott, C. et al., "FT–IR Spectroscopic Imaging Microscopy Using an MCT Focal–Plane Array Detector," CP430, *Fourier Transform Spectroscopy:*11th International Conference (ed. J.A. Haseth); 1998 The American Institute of Physics I–56396–746–4/98, pp. 377–378.

Marcott, Curtis et al., "Infrared Microspectroscopic Imaging of Biomineralized Tissues Using a Mercury–Cadmium–Telluride Focal–Plane Array Detector,": *Cellular and Molecular Biology*44(1), 109–115 (1998).

Snively, C.M. et al., "Application of Reat Time Mid–Infrared FTIR Imaging to Polymeric Systems. 1. Diffusion of Liquid Crystals into Polymers, "*Macromolecules,*vol. 31(11), pp. 3753–3755. (1998).

Wolfe, William L., "Introduction to Imaging Spectrometers, "Chapter 12, An Imaging Fourier Transform Spectrometer, Tutorial Texts in Optical Engineering, vol. TT25 (ed. D.C. O'Shea) SPIE Optical Engineering Press, pp. 66–69 (1997).

Wright N.A., et al., "The Design and Performance of a Mid–Infrared FT–IR Spectroscopic Imaging system," CP430, *Fourier Transform Spectroscopy:*11th International Conference (ed. J. A. de Haseth); 1998 The American Institute of Physics I–56396–746–4/98, pp. 371–372.

Sweedler; "High... Detectors" Analytical Chemistry, vol. 60, No. 4. Feb. 15, 1988.

IMAGING ATR SPECTROMETER

CROSS-REFERENCE TO RELATED APPLICATIONS

This application claims priority from U.S. Provisional Application No. 60/055,746, filed Aug. 15, 1997, of E. Michael Burka and Raul Curbelo, entitled "IMAGING ATR SPECTROMETER," the disclosure of which is incorporated by reference in its entirety for all purposes.

BACKGROUND OF THE INVENTION

Attenuated total (internal) reflection (ATR) spectroscopy is widely used to collect an absorption spectrum from samples that are too opaque for direct absorption measurements. One surface of an ATR crystal is placed in contact with a sample-under-test. An incident beam of radiation is directed through the ATR crystal so that it is totally internally reflected at the boundary between the ATR crystal and the sample-under-test. Some of the energy of the incident radiation is absorbed by the sample-under-test through evanescent coupling. The amount of absorption is representative of the molecular structure and/or the molecular species found in the sample-under-test. The reflected radiation, therefore, includes information from which an absorption spectrum for the sample-under-test is obtained.

Examples of systems for performing ATR spectroscopy include U.S. Pat. Nos. 3,393,603, 4,602,869, and 5,093,580. These systems are limited in that they typically employ a single-element detector and, therefore, are able to analyze only a small area of the sample-under-test at one time. Accordingly, some type of physical scanning is required to resolve the spatial distribution of molecular species in the sample by, for example, translating the sample on an XY stage through a field of view defined by the collecting and detecting optics, or translating the ATR relative to the sample.

Scanning the sample in this manner involves certain drawbacks and deficiencies. Specifically, the number of moving parts required to implement the scanning limits the speed and reliability of such systems. Furthermore, the signal to noise ratio obtainable by most FTIR (Fourier transform infrared) spectrometers requires that several measurements be taken at each point and averaged. The substantial averaging required makes such systems inherently slow.

SUMMARY OF THE INVENTION

The present invention provides a system, apparatus, and method for an imaging ATR spectrometer, and is characterized by higher speed and better spatial resolution than systems collecting an equivalent amount of data using conventional, non-imaging ATR techniques.

According to one aspect of the invention, apparatus includes a radiation source that provides an input beam of radiation, an ATR crystal, a focal plane array detector, at least one optical element directing and concentrating the input beam through the ATR crystal so that the input beam is totally internally reflected at a front surface of the ATR crystal, and at least one optical element collecting the reflected radiation and imaging the same onto the focal plane array detector. A wavelength-selective device such as an interferometer is disposed in the optical train. In a specific embodiment, the wavelength-selective device is disposed between the source and the ATR crystal. For interferometer-based embodiments, the result is a spectrally-multiplexed input beam. The ATR crystal is sufficiently large so that, in combination with a two-dimensional focal plane array detector, the present invention collects a spatially resolved absorption spectrum of a large area of the sample in a short time relative to conventional designs.

Another aspect of the present invention provides an imaging ATR micro-spectrometer including an ATR crystal, a focal plane array detector, a wavelength-selective device, a microscope objective, and an image forming optic. In one embodiment of this aspect of the invention, the microscope objective includes reflective optics for directing an input beam through the ATR crystal toward a sample, and for collecting the reflected radiation and directing the same towards the imaging optic.

A further understanding of the nature and advantages of the present invention may be realized by reference to the remaining portions of the specification and the drawings.

BRIEF DESCRIPTION OF THE DRAWINGS

FIGS. 4A and 4C are spectral measurements from two discrete points within the image of FIG. 4A.

DESCRIPTION OF THE SPECIFIC EMBODIMENTS

Figure 1:
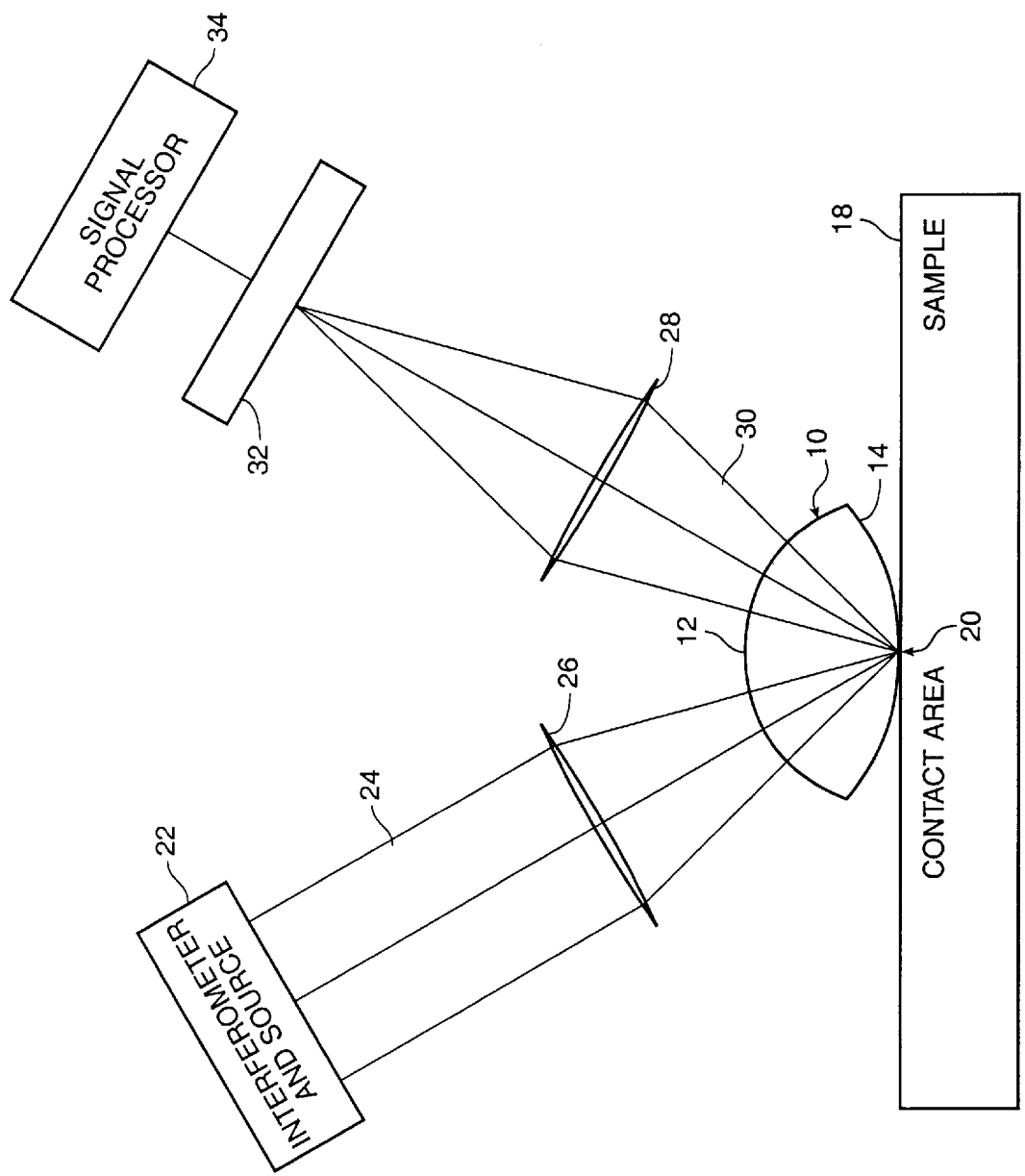
FIG. 1 is system diagram of an imaging ATR spectrometer according to a specific embodiment of the present invention.

FIG. 1 is a system diagram of an imaging ATR spectrometer according to the present invention. The specific embodiments are based on a Fourier transform spectrometer using a Michelson interferometer as a wavelength-selective element. Embodiments based on a dispersive spectrometer would use a grating or a prism as the wavelength-selective element. The central component of the imaging spectrometer is an internal reflection element (IRE) 10, which is shown in cross-section. IRE 10 has a rear surface 12 and a front surface 14, which contacts a sample 18 at a contact area 20. The details of IRE 10 are provided below.

An interferometer 22 produces a spectrally-multiplexed input beam 24 of broadband infrared radiation. Interferometer 22 is preferably of the type which includes a beamsplitter, at least one fixed mirror, and at least one moving mirror (e.g., a Michelson interferometer). In one embodiment of the present invention, an FTS-6000 spectrometer, available from Bio-Rad Laboratories, Inc., Hercules, Calif., was used. Those skilled in the art appreciate that other interferometer types can be substituted without departing from the scope of the present invention. For example, spectrometers incorporating acousto-optical tuned filters, Fabry-Perot scanning interferometers, or (as noted above) scanned grating devices could be used.

Focusing optics 26 (shown schematically as a lens) focuses input beam 24 through the rear surface 12 of IRE 10 towards contact area 20 such that the angle of incidence of input beam 24 is equal to or greater than the critical angle of IRE 10 (i.e., the angle at which light is totally internally reflected at the front face 14 of IRE 10). In this configuration, substantially all of the energy of input beam 24 is reflected when IRE 10 is not in contact with a sample 18. When the IRE is in contact with sample 18, however, some of the infrared energy from the input beam 24 is absorbed into the sample 18 through evanescent coupling. The amount of energy absorbed at each location of contact area 20 corresponds to the molecular structure and/or the molecular species found in the sample at that location. Thus, the reflected radiation includes information from which a spatially-resolved absorption spectrum of sample 18 can be obtained.

Collecting and imaging optics 28 (shown schematically as a lens) collects the reflected radiation 30 and images the same onto a two-dimensional focal plane array detector 32. Focal plane array detector 32 includes a two-dimensional array of detectors for measuring an intensity of incident radiation at discrete locations. Hence, focal plane array detector 32 provides intensity information for the radiation reflected from discrete points of contact area 20.

In one embodiment of the present invention, a 64×64 pixel mercury cadmium telluride (MCT) detector array, operated in photovoltaic mode, was successfully used. The particular focal plane detector array, Model J108, manufactured by Santa Barbara Research Center of Goleta, Calif., has a spectral response from 2.3 $\mu$m to 10 $\mu$m and a 61-$\mu$m center-to-center pixel spacing with >85% fill factor. In another embodiment, a 128×128 pixel indium antimonide (InSb) detector array, operated in photovoltaic mode, was successfully used. The particular detector array, Model SYS128-01, from the same vendor, has a spectral response from 1.0 $\mu$m to 5.5 $\mu$m and a 50-$\mu$m center-to-center pixel spacing with >85% fill factor. If the spectral range of interest is limited to wavelengths below 1.5 $\mu$m, an array of charge-coupled devices (CCDs) can be used.

One of ordinary skill will recognize that alternative embodiments of focal plane array detector 32 may be substituted according to the wavelength of the spectral information desired. For example, focal plane array detector 32 may be composed of platinum silicide detectors, silicon detectors, iridium silicide detectors, or detectors made from other materials exhibiting desirable characteristics at the frequency of interest.

Similarly, the optical train is appropriately tailored to the relevant portion of the infrared spectrum. In most cases, the optics will be reflective optics. So, although focusing optics 26 and collecting and imaging optics 28 are shown schematically as single-element lenses, one skilled in the art will recognize that these single-element lenses could be replaced with compound lenses, compound mirrors, or some combination thereof, without departing from the scope of the present invention.

Each pixel in focal plane array detector 32 provides a signal representing the time varying intensity of light falling on that pixel. As is well known, a Michelson interferometer has a moving mirror and a fixed mirror, with the input light split so that one portion encounters the moving mirror and one portion encounters the fixed mirror. The beam portions are recombined so that the optical interference between the two beam portions causes the intensity of each frequency component of the infrared beam to vary as a function of the component's optical frequency and the mirror position. The detector output represents the superposition of these components and, when sampled at regular distance intervals, provides an interferogram whose Fourier transform yields the desired spectrum. Thus each pixel in focal plane array detector 32 provides a signal that gives rise to an interferogram.

A signal processor 34 retrieves the intensity information obtained by focal plane array detector 32 and transforms the same into spectral image data. In one embodiment of the present invention, signal processor 34 includes signal conditioning electronics such as an analog to digital converter (not shown) and a digital computer (not shown). The digital computer calculates the two-dimensional Discrete Fourier Transform (DFT) of the intensity information to obtain the desired spectral image data by, for example, calculating the Fast Fourier Transform (FFT) of the interferograms. The digital computer also includes memory for storing various information including, but not limited to, intensity information, and spectral image data. The spectral image data may then be retrieved from memory and further manipulated using known spectroscopic, chemometric, and image processing techniques. U.S. Pat. No. 5,262,635 to Curbelo, the entire disclosure of which is hereby incorporated by reference for all purposes, provides additional information on Fourier transform spectrometers and some of the signal conditioning and signal processing that are performed.

Figure 2:
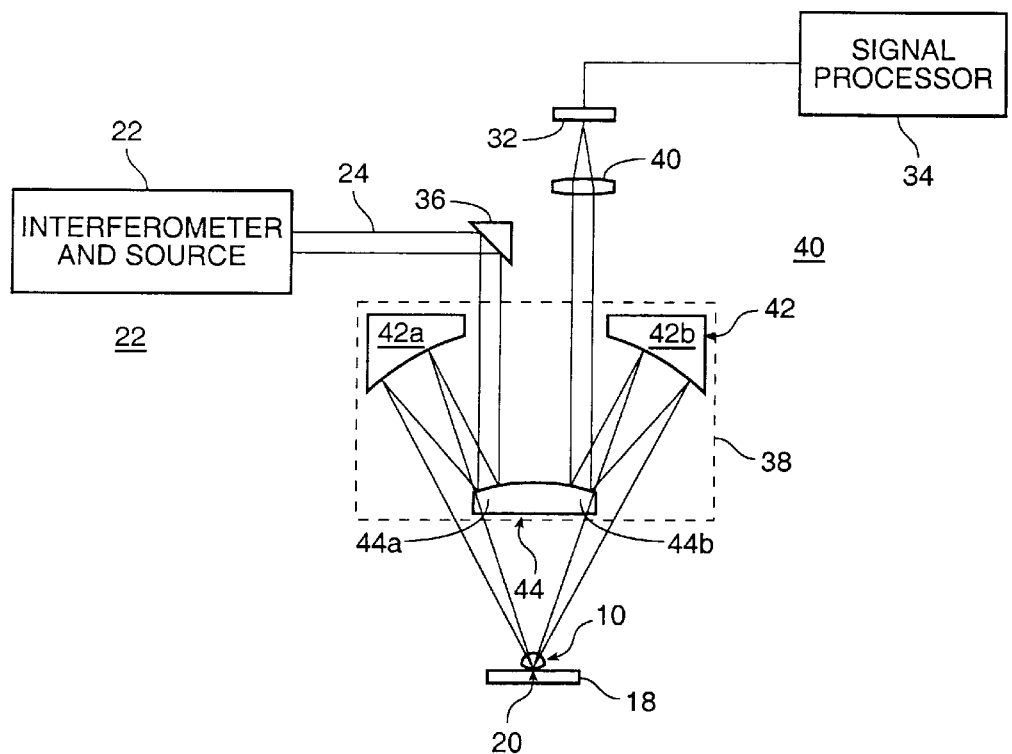
FIG. 2 is a diagram of an imaging ATR microspectrometer according to a specific embodiment of the present invention.

FIG. 2 is a system diagram of an imaging ATR microspectrometer according to a specific embodiment of the present invention. Elements which are identical to those shown in FIG. 1 are numbered identically. Interferometer 22 produces the input beam 24 of radiation. A mirror optic 36 directs input beam 24 into a reflective microscope objective 38. Microscope objective 38 focuses the input beam 24 through IRE 10 to contact area 20 of the sample 18 such that the angle of incidence of input beam 24 is equal to or greater than the critical angle of IRE 10. Different portions of the surfaces of mirrors in microscope objective 38 collect the reflected radiation 30 and direct the same towards an image-forming optic 40. Image-forming optic 40 images the reflected radiation 30 onto focal plane array detector 32 as described above.

Microscope objective 38 is a reflective optic of a type well-known in the art, having a concave primary mirror 42 and a convex secondary mirror 44, each having rotational symmetry about a common axis. One half of each mirror is used for focusing incoming radiation and the other half of each is used for collecting radiation after it has interacted with the sample. Specifically, primary mirror 42 has portions 42a and 42b while secondary mirror 44 has portions 44a and 44b.

Radiation (input beam 24) is reflected from mirror optic 36 and encounters portions 44a and 42a of the secondary and primary mirrors, respectively, which focus the input beam 24 of radiation towards contact area 20 through IRE 10 as described above. Portions 42b and 44b of the primary and secondary mirrors collect the radiation reflected from the sample and direct it to image-forming optic 40.

Image-forming optic 40 is shown as a single-element lens. One skilled in the art, however, will recognize that image-forming optic 40 may be a compound lens, a compound mirror, or some combination thereof. In one embodiment of the present invention, image-forming optic 40 is a lens that also performs the functions of magnification and distortion correction/elimination. Lenses are available in various infrared transmitting materials to cover the entire wavelength range to which current array detectors are sensitive. Typical lens materials are zinc selenide, silicon, and germanium.

Figure 3A:
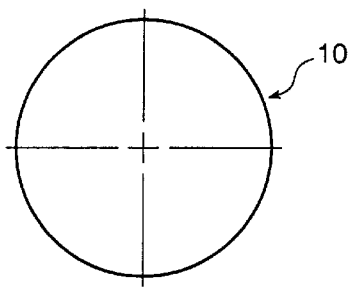
FIGS. 3A and 3B are a bottom and side view of an internal reflection element (i.e., ATR crystal) according to a specific embodiment of the present invention.
Figure 3B:
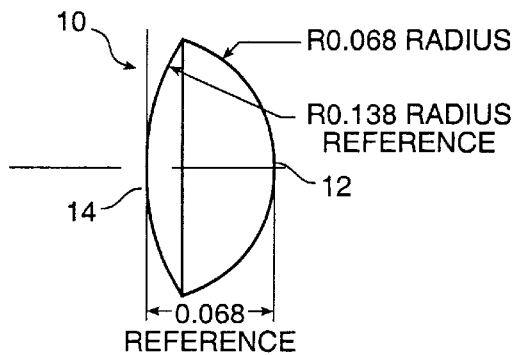

FIGS. 3A and 3B are bottom and side views, respectively, of a specific embodiment of the ATR crystal (i.e., IRE 10) according to the present invention. IRE 10 may be made from many materials. For example, in one embodiment of the present invention, IRE 10 is made from germanium. In an alternative embodiment, IRE 10 can be made from silicon, zinc selenide, or diamond.

In the specific implementation, IRE 10 has a diameter of 0.132 inches. IRE 10 includes a front surface 14 and a rear surface 12 each having a spherical curvature. The center of curvature of the rear surface 12 lies in the front surface 14 (i.e., the thickness of IRE 10 is equal to the radius of curvature of rear surface 12). This configuration minimizes the refraction of input beam 24 and reflected radiation 30 at the rear surface 12, thereby reducing the amount of optical aberration in the system.

In a specific embodiment of the invention, the depth of IRE 10 is 0.068 inches, the radius of curvature for the front surface 14 is 0.138 inches, and the radius of curvature of the rear surface 12 is 0.068 inches. The center of the radius of curvature of the rear surface 12 is centered on the front surface 14 to within a tolerance of 0.001 inches. The vertex of the front surface 14 is within a tolerance of 0.001 inches radially and 0.002 inches axially of the center of the rear surface radius. The surface figure is better than 0.00005 inches, or two wavelengths when measured with a Helium-Neon laser reference.

Figure 4A:
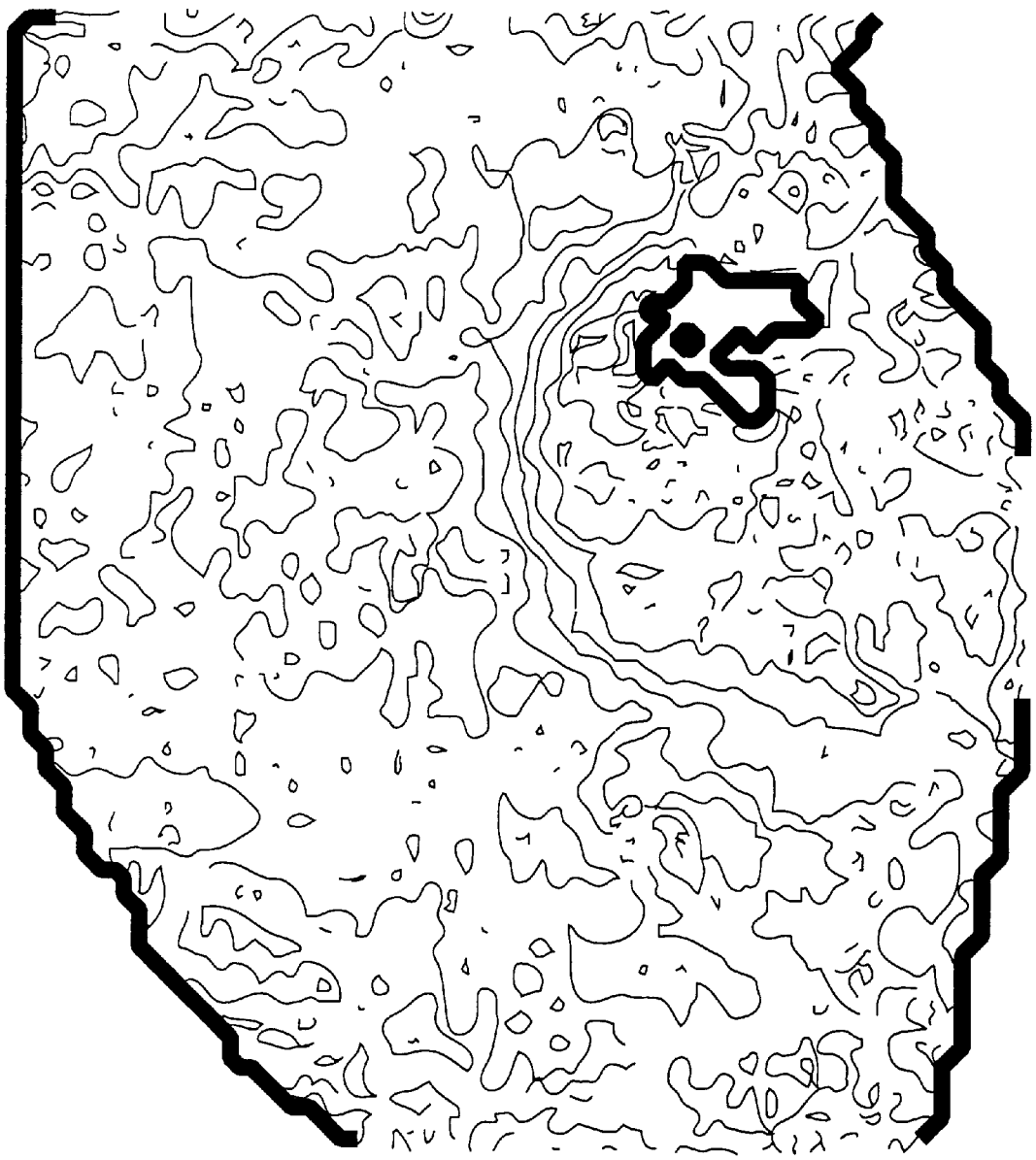
FIG. 4A is a spectral image of a spool of epoxy resin fiber obtained with the imaging ATR micro-spectrometer of the present invention.
Figure 4B:
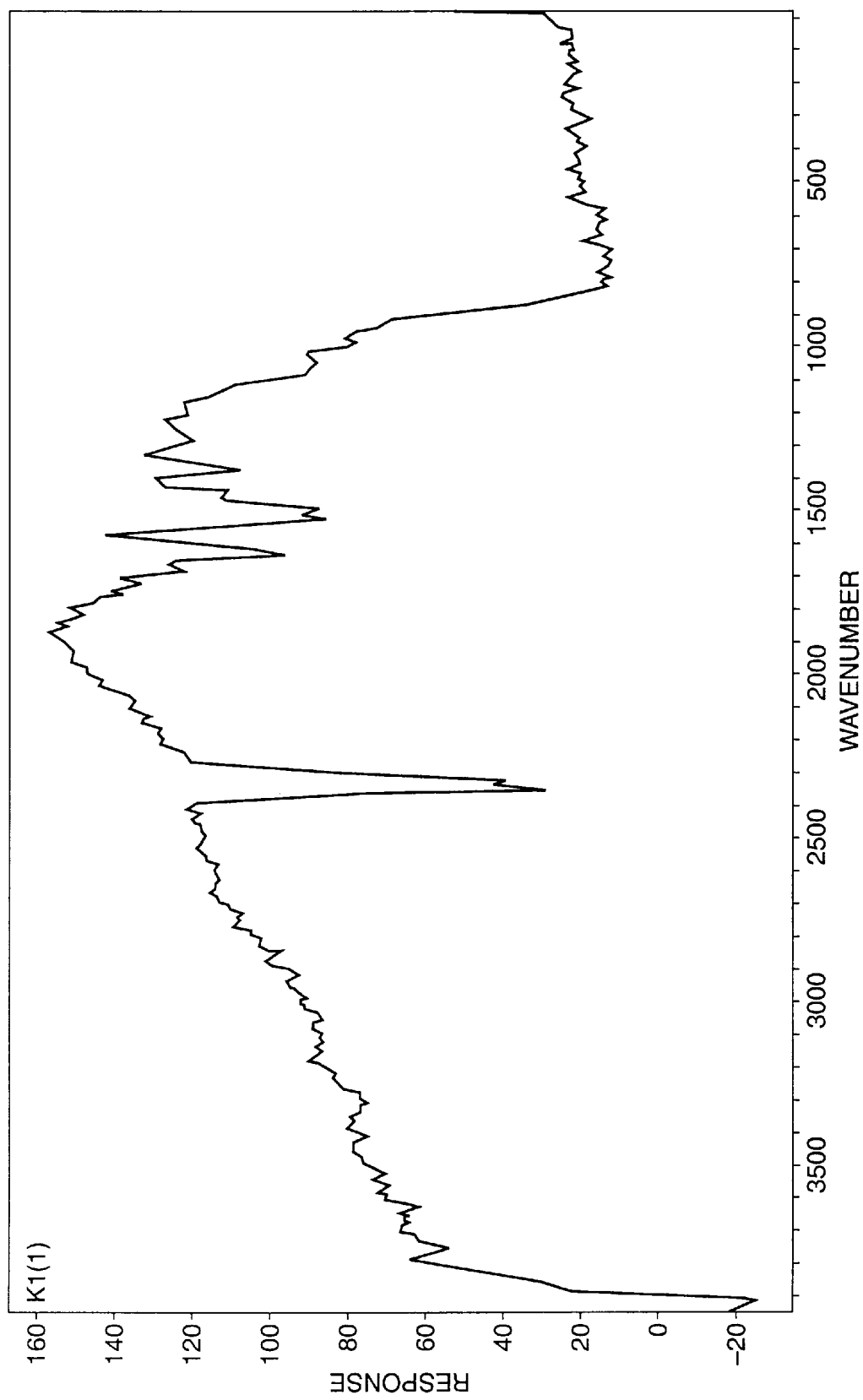
Figure 4C:
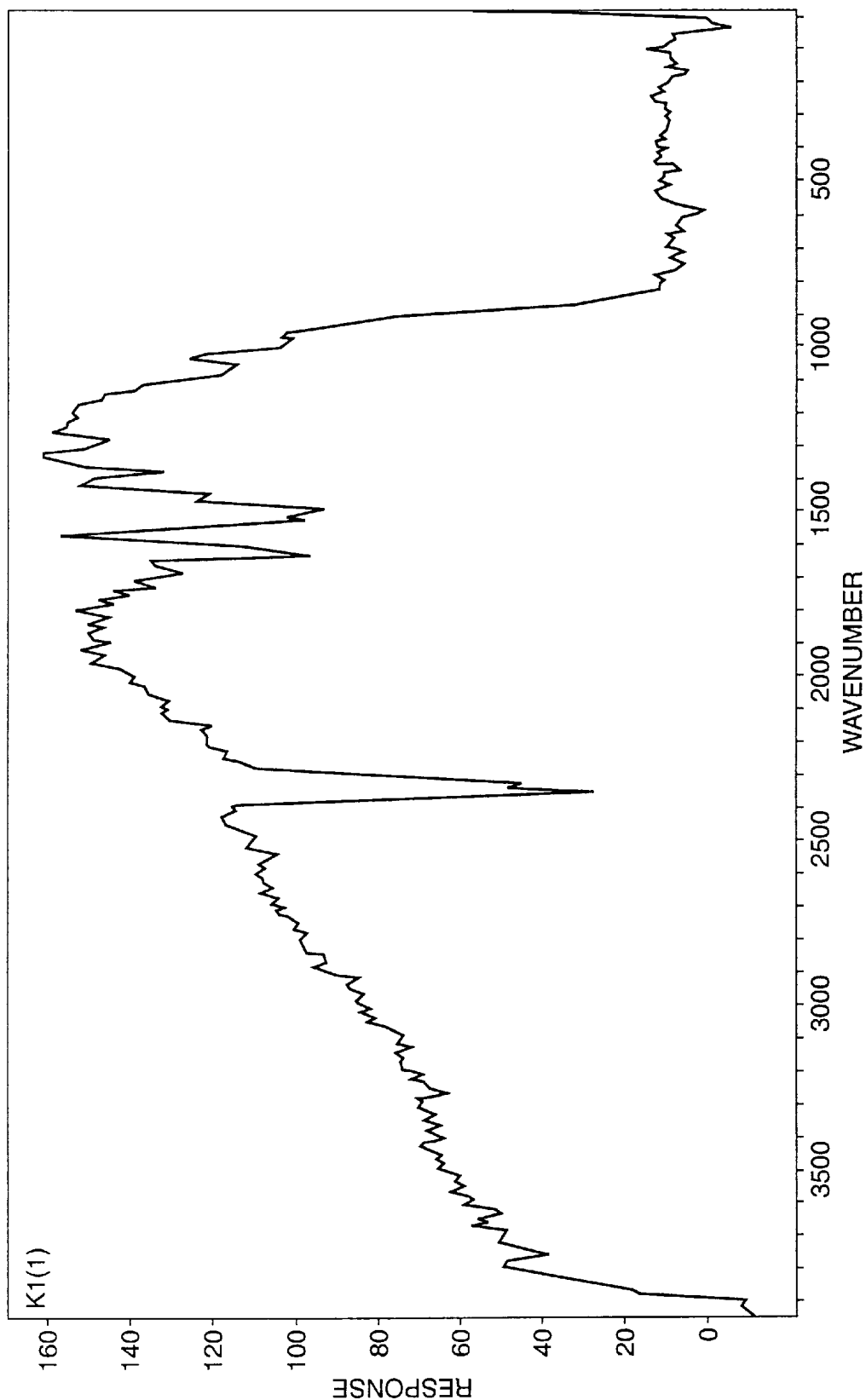

FIG. 4A is a spectral image of a spool of epoxy resin fiber obtained with the imaging ATR micro-spectrometer of the present invention. FIGS. 4B and 4C are spectral measurements from two discrete points within the image of FIG. 4A. A mercury cadmium telluride array was used to collect these data. These are single beam data and have not been normalized to background data. FIG. 4A shows spectral contour lines at 950 cm$^{-1}$ over an area of approximately 400 microns square. The irregular area in the upper right field is more brightly illuminated than the surrounding area, and the pixels there are saturated.

FIGS. 4B and 4C are the single beam spectra from two points in the field of FIG. 4A. FIG. 4B shows the spectral response from the pixel in row 26, column 28. FIG. 4C shows the spectral response from the pixel in row 32, column 28. The sample areas imaged onto these pixels are separated by 60 microns. FIG. 4B shows more absorbance by the sample in the 1200–1400 cm$^{-1}$ band than FIG. 4C.

The spatial resolution of a single pixel ATR is equal to the contact area. In a microscope ATR, this is typically 100 $\mu$m across. In imaging micro-ATR of the invention, a 10-$\mu$m resolution is achieved with the MCT array and 5-$\mu$m resolution with the InSb array.

In conclusion, it can be seen that the imaging ATR spectrometer of the present invention provides higher speed and better spatial resolution than a system which collects an equivalent amount of data using conventional non-imaging ATR systems.

While the above is a complete description of preferred embodiments of the invention, it is appreciated by those in the art that various alternatives, modifications, and equivalents may be used. For example, the configuration described above, where the output from the interferometer is input to the microscope, has the advantage that the invention can be used with any general purpose spectrometer, and does not require a dedicated spectrometer. However, the invention would also work if the unmodulated infrared source illuminated the sample and the interferometer (modulator) were located in the output path. Therefore, the above description should not be taken as limiting the scope of the invention which is defined by the appended claims.

What is claimed is:

1. An imaging attenuated total reflection (ATR) spectrometer comprising:

a radiation source;

an internal reflection element (IRE) having a front surface and a rear surface, said front surface including a contact area for engaging a sample-under-test;

a two-dimensional focal plane array detector for detecting radiation incident upon and reflected from discrete locations of said contact area;

means for directing and concentrating radiation from said radiation source through said rear surface of said IRE towards said contact area such that an angle of incidence of said input beam at said front surface is equal to or greater than a critical angle for said IRE;

means for collecting reflected radiation from said contact area and for imaging said reflected radiation onto said two-dimensional focal plane array detector, said reflected radiation including information relating to a spatial distribution of reflected energies; and a wavelength-selective element coupled to intercept radiation traveling between said radiation source and said two-dimensional focal plane array detector to effect spectrally selective modulation of radiation intercepted by said wavelength-selective element.

2. The imaging ATR spectrometer of claim 1, further comprising a signal processor coupled to said focal plane array detector for obtaining said spatial distribution information from said two-dimensional focal plane array detector.

3. The imaging ATR spectrometer of claim 1, wherein:

said means for directing and concentrating includes one or more lens elements; and said means for collecting reflected radiation and for imaging said reflected radiation includes one or more lens elements.

4. The imaging ATR spectrometer of claim 1, wherein:

said means for directing and concentrating includes one or more reflective elements; and said means for collecting reflected radiation and for imaging said reflected radiation includes one or more reflective elements.

5. The imaging ATR spectrometer of claim 1, wherein said rear surface of said IRE is convex and has a spherical curvature whose center of curvature lies on said front surface of said IRE.

6. The imaging ATR spectrometer of claim 5, wherein said front surface of said IRE is convex and has a spherical curvature whose radius of curvature is substantially longer than a rear surface radius.

7. The imaging ATR spectrometer of claim 1, wherein said spectrally-selective element is an interferometer located between said radiation source and said IRE so as to produce a spectrally-multiplexed input beam of radiation to said IRE.

8. An imaging attenuated total reflection (ATR) spectrometer comprising:

a radiation source;

an internal reflection element (IRE) having a front surface and a rear surface, said front surface including a contact area for engaging a sample-under-test;

a two-dimensional focal plane array detector for detecting radiation incident upon and reflected from discrete locations of said contact area;

a first optical system adapted and positioned to direct said input beam through said rear surface of said IRE and toward said contact area such that an angle of incidence of said input beam at said front surface is equal to or greater than a critical angle for said IRE;

a second optical system adapted and positioned to collect reflected radiation from said contact area and to image said reflected radiation onto said two-dimensional focal plane array detector, said reflected radiation including information relating to a spatial distribution of reflected energies; and an interferometer coupled to intercept radiation traveling between said radiation source and said two-dimensional focal plane array detector to effect spectrally selective modulation of radiation intercepted by said interferometer.

9. The imaging ATR spectrometer of claim 8, wherein said interferometer is of the type including a beam splitter, at least one fixed mirror, and at least one movable mirror.

10. The imaging ATR spectrometer of claim 8, wherein said radiation source comprises a broadband infrared light source.

11. The imaging ATR spectrometer of claim 8, wherein:

said first optical system includes one or more lens elements; and said second optical system includes one or more lens elements.

12. The imaging ATR spectrometer of claim 8, wherein:

said first optical system includes one or more reflective elements; and said second optical system includes one or more reflective elements.

13. The imaging ATR spectrometer of claim 8, wherein said rear surface of said IRE is convex and has a spherical curvature whose center of curvature lies on said front surface of said IRE.

14. The imaging ATR spectrometer of claim 13, wherein said front surface of said IRE is convex and has a spherical curvature whose radius of curvature is substantially longer than a rear surface radius.

15. A method of obtaining a spectral absorption image of a sample comprising the steps of:

positioning an ATR crystal over a portion of the sample and in contact with same so that a contact area between the ATR crystal and the sample is defined;

irradiating said contact area by directing a beam of radiation originating from a source through said ATR crystal and toward said contact area at the angle of incidence equal to or greater than the critical angle of the ATR crystal;

collecting reflected radiation from said contact area, the reflected radiation including spatial information;

imaging said reflected radiation from said contact area onto a two-dimensional array of detectors; and interposing a wavelength-selective element between said source and said two-dimensional array of detectors to provide spectral information at different locations of said contact area.

16. The method of claim 15 further comprising the steps of:

converting data collected by said two-dimensional array of detectors into the spectral absorption image.

17. The method of claim 16, wherein said step of converting comprises the steps of:

retrieving intensity information from said two-dimensional array of detectors; and calculating a Fourier transform representation of said intensity information.

18. An imaging attenuated total reflection (ATR) microspectrometer comprising:

a radiation source;

an internal reflection element (IRE) having a front surface and a rear surface, said front surface including a contact area for engaging a sample-under-test;

a two-dimensional focal plane array detector for detecting radiation incident upon and reflected from discrete locations of said contact area;

a microscope objective, wherein said IRE is at a focus of said microscope objective;

means for directing said input beam of radiation into said microscope objective;

an image-forming optic;

wherein said microscope objective is positioned and configured to focus said input beam of radiation through said rear surface of said IRE towards said contact area, to collect said reflected radiation, and to direct said reflected radiation towards said image-forming optic;

wherein said image-forming optic images said reflected radiation onto said two dimensional focal plane array detector, said reflected radiation including information relating to a spatial distribution of reflected energies; and an interferometer coupled to intercept radiation traveling between said radiation source and said two-dimensional focal plane array detector to effect spectrally selective modulation of radiation intercepted by said interferometer.

* * * * *